(12) United States Patent
Saevecke et al.

(10) Patent No.: US 11,628,100 B2
(45) Date of Patent: Apr. 18, 2023

(54) ARTICLES HAVING AN ACQUISITION LAYER WITH STRETCH OPENINGS AND PROCESSES TO MAKE THEM

(71) Applicant: The Procter & Gamble Company, Cincinnati, OH (US)

(72) Inventors: Dirk Saevecke, Wiesbaden (DE); Julien René Garcia, Frankfurt (DE); Maike Siemons, Oberursel (DE)

(73) Assignee: The Procter & Gamble Company, Cincinnati, OH (US)

( * ) Notice: Subject to any disclaimer, the term of this patent is extended or adjusted under 35 U.S.C. 154(b) by 1035 days.

(21) Appl. No.: 16/387,579

(22) Filed: Apr. 18, 2019

(65) Prior Publication Data
US 2019/0328588 A1    Oct. 31, 2019

(30) Foreign Application Priority Data

Apr. 27, 2018   (EP) .................................... 18169902

(51) Int. Cl.
*A61F 13/15*     (2006.01)
*A61F 13/535*    (2006.01)
(Continued)

(52) U.S. Cl.
CPC ...... *A61F 13/535* (2013.01); *A61F 13/15699* (2013.01); *A61F 13/51104* (2013.01); *A61F 13/53708* (2013.01); *A61F 13/53747* (2013.01); *A61F 13/53756* (2013.01); *A61F 13/15747* (2013.01); *A61F 13/472* (2013.01);
(Continued)

(58) Field of Classification Search
CPC .............. A61F 13/535; A61F 13/15699; A61F 13/5114; A61F 13/53708; A61F 13/53747; A61F 13/53756; A61F 13/15747; A61F 13/472; A61F 13/49; A61F 2013/49053; A61F 2013/53721
See application file for complete search history.

(56) References Cited

U.S. PATENT DOCUMENTS

| 5,397,316 | A | * | 3/1995 | LaVon | ................ | A61F 13/5376 |
| | | | | | | 604/382 |
| 5,628,097 | A | * | 5/1997 | Benson | ..................... | B26F 1/00 |
| | | | | | | 28/165 |

(Continued)

FOREIGN PATENT DOCUMENTS

WO   WO2018004564 A1   1/2018

OTHER PUBLICATIONS

Extended European Search Report and Search Opinion; Application No. 18169902.6-1102; dated Nov. 13, 2018; 10 pages.
(Continued)

*Primary Examiner* — Jacqueline F Stephens
(74) *Attorney, Agent, or Firm* — Christian M. Best (57) ABSTRACT

An absorbent article such as a diaper comprising an acquisition layer with one or more longitudinally-extending stretch openings is provided. The stretch openings may be obtained by slitting and stretching an acquisition layer material. The topsheet forms recesses at the wearer-facing surface of the absorbent article as it folds inside the stretch openings. The stretch openings may provide a three dimensional profile on the wearer-facing side of the absorbent article in a simple and cost effective manner.

10 Claims, 3 Drawing Sheets

(51) Int. Cl.
*A61F 13/511* (2006.01)
*A61F 13/537* (2006.01)
A61F 13/472 (2006.01)
A61F 13/49 (2006.01)

(52) U.S. Cl.
CPC ..... *A61F 13/49* (2013.01); *A61F 2013/49053* (2013.01); *A61F 2013/53721* (2013.01)

(56) References Cited

U.S. PATENT DOCUMENTS

| | | | |
|---|---|---|---|
| 6,632,504 B1* | 10/2003 | Gillespie | D04H 3/16 442/352 |
| 9,789,011 B2 | 10/2017 | Roe et al. | |
| 9,987,176 B2 | 6/2018 | Roe et al. | |
| 2007/0073254 A1 | 3/2007 | Ponomarenko et al. | |
| 2012/0136329 A1 | 5/2012 | Carney | |
| 2012/0316526 A1 | 12/2012 | Rosati et al. | |
| 2013/0143020 A1* | 6/2013 | Wood | B32B 5/022 428/220 |
| 2015/0065981 A1 | 3/2015 | Roe et al. | |
| 2016/0074237 A1* | 3/2016 | Rosati | A61F 13/53 156/219 |
| 2017/0165396 A1 | 6/2017 | Turner | |
| 2018/0049928 A1 | 2/2018 | Quincy, III et al. | |

OTHER PUBLICATIONS

International Search Report and Written Opinion; Application Ser. No. PCT/US2019/025303; dated Oct. 14, 2019, 15 pages.

* cited by examiner

ARTICLES HAVING AN ACQUISITION LAYER WITH STRETCH OPENINGS AND PROCESSES TO MAKE THEM

CROSS REFERENCE TO RELATED APPLICATION

This application claims priority, under 35 U.S.C. § 119, to European Patent Application Serial No. 18169902.6, filed on Apr. 27, 2018, the entire disclosure of which is hereby incorporated by reference herein.

FIELD OF THE INVENTION

The invention relates to personal hygiene absorbent articles that are placed in the crotch of a wearer to absorb body exudates, and processes to make them. Such articles include, but are not limited to, baby taped diapers, baby pant-like diapers (including training pants), feminine pads and adult incontinence products.

BACKGROUND OF THE INVENTION

Absorbent articles for personal hygiene are designed to absorb and contain body exudates, in particular large quantity of urine. These absorbent articles typically comprise a topsheet on the wearer-facing side that is permeable to the fluid and feels soft on the wearer's skin, a backsheet on the garment-facing side for protecting the wearer's clothes, and in-between an absorbent core for absorbing and retaining the fluid.

Absorbent articles may also comprise one or more layers between the topsheet and the absorbent core whose function is to quickly acquire the fluid away from the topsheet of the article and distribute it to the underlying absorbent core. These layers are sometimes designated as acquisition layers, distribution layers or acquisition-distribution layers. For simplification, these will be referred herein as acquisition layers. A simple acquisition layer construction consists of a discrete layer of a nonwoven material disposed directly under the topsheet and comprising synthetic fibers, for example a thermobonded or through air bonded nonwoven. Acquisition systems comprising several layers are also used in some diaper products.

Absorbent articles may benefit from having a three dimensional surface on their wearer-facing surface. The presence of channels at the surface of the article may for example help keeping the skin of the user dry, among other benefits such as liquid handling, or pasty bowel moment handling. Absorbent articles comprising macroscopic channels in the absorbent core (e.g. WO2012/170778A1, Rosati et al., WO 2014/200794 A1, Bianchi et al.) and more recently in an acquisition layer (e.g. WO2015/031225A1, Roe et al.) have been proposed.

There is a need for a cost efficient and simple way to provide a three dimensional profile to the wearer-facing surface of absorbent articles.

SUMMARY OF THE INVENTION

In one aspect, the present invention is directed at an absorbent article for personal hygiene having a wearer-facing side, a garment-facing side and a longitudinal axis, such as a taped diaper or a diaper pant. The article comprises a liquid permeable topsheet on the wearer-facing side, a liquid impermeable backsheet on the garment-facing side, an absorbent core between the topsheet and the backsheet; and an acquisition layer between the topsheet and the absorbent core. The acquisition layer comprises one or more longitudinally-extending stretch openings. The stretch openings provide a three dimensional profile on the wearer-facing side of the article in a simple and cost effective manner. In another aspect, the present invention is for a process for making articles according to the invention. The stretch openings can be obtained by slitting or otherwise weakening discrete areas of an acquisition layer material to form openable areas which are then then opened by stretching to form the stretch openings. Further optional features and advantages of the invention are disclosed in the attached claims and following description.

For ease of discussion, the examples of the invention are discussed below with reference to these Figures and the numerals referred therein, however these are not intended to limit the scope of the claims unless specifically indicated.

DETAILED DESCRIPTION OF THE INVENTION

General Description of an Absorbent Article 20

Figure 1:
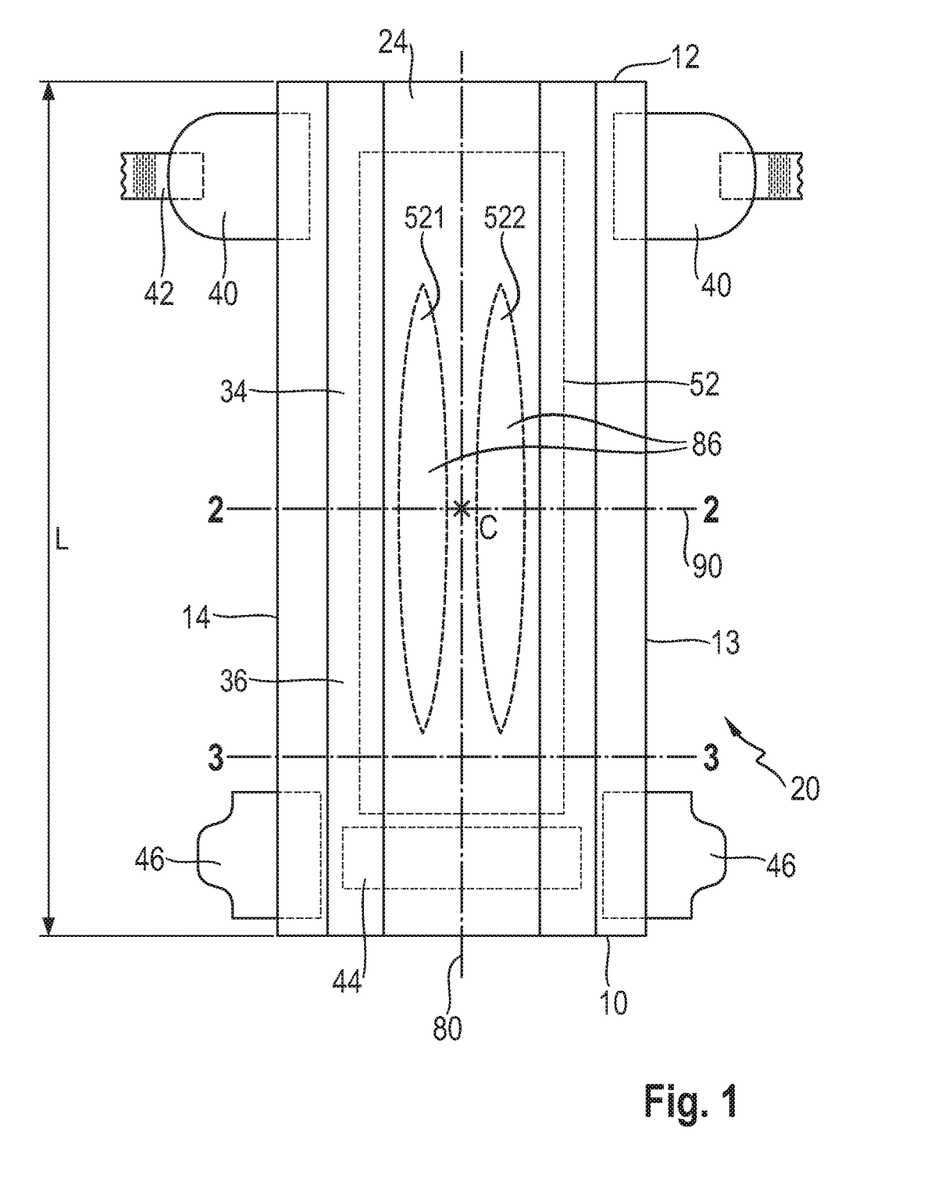
FIG. 1 is a top view of the wearer-facing side of a taped diaper which has been pulled flat and comprising a pair of stretch openings.
Figure 2:
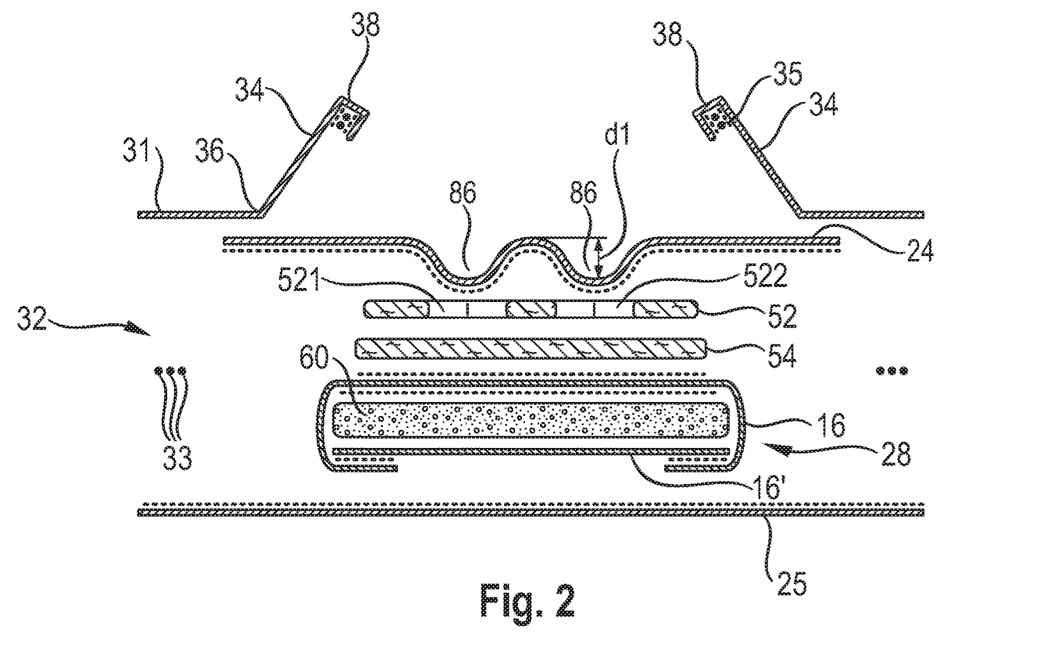
FIG. 2 shows a schematic transversal cross-section of the taped diaper of FIG. 1 in the area of the stretch openings.

An exemplary absorbent article according to the invention in the form of a baby taped diaper 20 is represented in FIGS. 1-2. FIG. 1 is a top plan view of the wearer-facing side of an exemplary diaper in a flat-out state, with the acquisition layer 52 and the stretch openings 521, 522 shown in dotted lines. FIG. 2 is a cross-sectional view showing some of the different layers of the diaper of FIG. 1. This diaper 20 is shown for illustration purpose only, as the invention may be used for making a wide variety of diapers or other absorbent articles such as pant-like diapers, training pants, adult incontinence pants or feminine sanitary pads. In the following description the term diaper and absorbent article are used interchangeably.

As illustrated in FIG. 1, the absorbent article 20 comprises a front edge 10, a back edge 12, and two longitudinally-extending side (lateral) edges 13, 14. The front edge 10 is the edge of the article which is intended to be placed towards the front of the user when worn, and the back edge 12 is the opposite edge. The absorbent article is notionally divided by a longitudinal axis 80 extending along a longitudinal direction from the middle of the front edge to the middle of the back edge of the article and dividing the article in two substantially symmetrical halves relative to this axis, when viewing the article from the wearer-facing side in a flat out configuration, as exemplarily shown in FIG. 1. If some parts of the article are under tension due to elasticized components, the article may be typically flattened using clamps along the periphery of the article and/or a sticky surface, so that the article can be pulled taut so as to be substantially flat. Closed articles such as pant-like baby diapers, training pants for small children, or adult incontinent pants may be cut open along the side seams to apply them on a flat surface, as is known in the art. Unless otherwise indicated, dimensions and areas disclosed herein apply to the article in this flat-out configuration.

The article has further a length L as measured along the longitudinal axis 80 from the front edge 10 to the back edge 12 of the article. The absorbent article can also be notionally divided by a transversal axis 90 at half the length L of the article. The transversal axis 90 is perpendicular to the longitudinal axis 80. The intersection of the longitudinal axis 80 and the transversal axis 90 is defined herein as the centerpoint C of the article. The article can be further notionally divided in three regions having equal length of a third of L along the longitudinal axis: a front region extending from the front edge 10 towards the crotch region for a third of L, a crotch region in the middle third of the diaper, and a back region extending from the crotch region to the back edge 12 of the article for the remaining third of L. All three regions are of equal length measured on the longitudinal axis, when the article is in such a flat state. The front region, crotch region, back region and longitudinal and transversal axis are defined herein notionally, that is they are typically not materialized in the real diapers, but are useful to describe the positions of various components of the invention relative to each other and the diaper.

The absorbent article 20 comprises a liquid-permeable topsheet 24, a liquid-impermeable backsheet 25 and an absorbent core 28 between the topsheet and the backsheet. The absorbent core typically comprises an absorbent material 60 enclosed in a core wrap having a top side 16 and bottom side 16'. The absorbent material 60 defines an absorbent layer having a deposition area within the core wrap.

The absorbent article further comprises one or more intermediate layers between the topsheet and the absorbent core. According to the present invention, the absorbent article comprises an acquisition layer 52 between the topsheet and the absorbent core, the acquisition layer comprising at least one (one, two, or more) longitudinally-extending stretch openings. The article may comprise in particular a pair of stretch openings 521, 522 disposed symmetrically relative to the longitudinal axis, as exemplarily illustrated in FIG. 1. In the following disclosure, for simplicity, the plural form "stretch openings" will be used to mean "one or more stretch openings, in particular at least a pair of stretch openings", unless specifically indicated otherwise.

The stretch openings are substantially free of the acquisition material forming the rest of the acquisition layer. A portion of the topsheet can thus at least partially reside within in at least one of the stretch openings and form recesses 86 on the wearer-facing side of the article, providing a three dimensional profile at the wearer-facing side of the article. The topsheet may further be advantageously attached through the stretch openings to an underlying layer (for example an additional (second) acquisition layer 54 if present, or directly the top side of the core wrap) by gluing, heat bonding or otherwise. Attaching the topsheet to an underlying layer through the stretch openings can provide a more visible and more permanent three-dimensional profile at the surface of the article. The adhesive between the layers is represented in the Figures by the dotted black lines. The recesses 86 can be perceived by sight and/or touch from the wearer-facing side of the article, even if the recesses have a relatively small depth. The recesses may have a depth of at least 0.25 mm, or at least 0.5 mm, or are least 1.0 mm and up to 6.0 mm, or up to 5 mm, or up to 4 mm and any ranges obtained by combining any one of the lower values with any one of the upper values. The recesses 86 can provide a conduit at the surface of the article for better air circulation and breathability. However, even if the topsheet is not attached through the stretch openings to an underlying layer, the topsheet 24 will typically form recesses 86 by conforming to the stretch openings.

The absorbent article can optionally but advantageously comprise an additional acquisition layer 54 which may be comprised of a single piece of acquisition material. This second, additional acquisition material layer may be disposed as represented on FIG. 2 between the absorbent core and the (first) acquisition layer comprising the stretch openings. The second acquisition layer is optional.

The wearer-facing side of the article is principally formed by the topsheet 24. A lotion (not represented) may be present, typically in longitudinally-extending slots, directly on the topsheet. Some typical diaper components are represented in the Figures, such as elasticized gasketing cuffs 32 (also called outer cuffs) comprising elastics strands 33, upstanding barrier leg cuffs 34 (inner cuffs) comprising elastic strands 35 as is known in the art. Typically each cuff may typically comprise from 1 to 4 elastic strands. In taped diapers, a pair of fastening tabs 42 and a landing zone 44 are typically provided. The absorbent article may also comprise other typical components, which are not represented in the Figures, such as a back elastic waist feature, a front elastic waist feature, transverse barrier cuffs, a wetness indicator between the backsheet and the absorbent core that changes color when contacted with urine, etc.

Acquisition Layer 52

The absorbent article comprises an acquisition layer 52 comprising one or more stretch openings 521, 522. The acquisition layer 52 may be typically placed directly under the topsheet 24. The acquisition layer can typically quickly acquire the fluid away from the topsheet so as to provide a good feeling of dryness for the wearer. The article may optionally comprise a second acquisition layer 54, which may be typically disposed between the acquisition layer 52 and the absorbent core 28 as shown, but alternatively the second acquisition layer could also be disposed between the first acquisition layer and the topsheet. In the present disclosure, the term "acquisition layer" will refer to the (first) acquisition layer comprising the stretch openings, and if present the second acquisition layer 54 will be referred to as additional or second acquisition layer.

The acquisition layer is typically a nonwoven. As used herein, the terms "nonwoven material", "nonwoven layer", "nonwoven web" or more simply "nonwoven" are defined (ISO 9092) as a sheet of fibers, continuous filaments, or chopped yarns of any nature or origin, that have been formed into a web by any means, and bonded together by any means, with the exception of weaving or knitting. Felts obtained by wet milling are not nonwovens. The fibers may be of natural or synthetic origin and may be staple or continuous filaments or be formed in situ. Commercially available fibers have diameters ranging from less than about 0.001 mm to more than about 0.2 mm and they come in several different forms such as short fibers (known as staple, or chopped), continuous single fibers (filaments or monofilaments), untwisted bundles of continuous filaments (tow), and twisted bundles of continuous filaments (yarn). Nonwoven webs can be formed by many processes such as meltblowing, spunbonding, solvent spinning, electrospinning, carding and airlaying. The basis weight of nonwoven webs is usually expressed in grams per square meter (g/m² or gsm). Nonwovens can be manufactured outside the converting line and stored and transported as a roll of material. The materials may then be unrolled into a stream of continuous material on the converting line, which is then processed to be made into an acquisition layer according to the invention.

A typical acquisition layer that may be used in the present invention is a bonded carded web, in particular a through-air bonded carded web ("TABCW"). "Bonded carded web" refers to webs that are made from staple fibers that are sent through a combing or carding unit, which breaks apart and aligns the staple fibers in the machine-direction to form a generally machine-direction-oriented fibrous nonwoven web. This web is then drawn through a heated drum, creating bonds throughout the fabric without applying specific pressure (through air bonding process). A TABCW material provides a low density, lofty through-air bonded carded web. The web may for example have a basis weight at from about 15 gsm to about 120 gsm (gram per square meter), in particular from about 30 gsm to about 80 gsm. A TABCW material can for example comprise from about 3 to about 20 denier staple fibers. Examples of such TABCW are disclosed in WO2000/71067 (KIM DOO-HONG et al.). TABCW are available directly from all usual suppliers of nonwoven webs for use in absorbent articles, for example Fitesa Ltd or Fiberweb Technical Nonwovens.

The acquisition material may also be a latex bonded nonwoven. Examples of such acquisition layers are disclosed in U.S. Pat. No. 7,786,341 (Schneider et al.). Carded, resin-bonded nonwovens may be used, in particular where the fibers used are solid round or round and hollow PET staple fibers (example 50/50 or 40/60 mix of 6 denier and 9 denier fibers). Further useful nonwovens are described in U.S. Pat. No. 6,645,569 (Cramer et al.), U.S. Pat. No. 6,863,933 (Cramer et al.), U.S. Pat. No. 7,112,621 (Rohrbaugh et al.), US2003/148684 (Cramer et al.) and US2005/008839 (Cramer et al.). The acquisition layer may be stabilized by a latex binder, for example a styrene-butadiene latex binder (SB latex). Processes for obtaining such latex are known, for example, from EP 149880 (Kwok) and US 2003/0105190 (Diehl et al.). The binder may typically be present in the acquisition layer in amount ranging from about 12% to about 50%, for example about 30%, by total weight of the acquisition layer. SB latex is available under the trade name GENFLO™ 3160 (OMNOVA Solutions Inc.; Akron, Ohio).

An alternative acquisition material may for example be a SMS (spunmelt) nonwoven material. Spunmelt is a generic term describing the manufacturing of nonwoven webs directly from thermoplastic polymers. It encompasses two processes and the combination of both: spunbond (also known as spunlaid) nonwoven and meltblown nonwoven. In a spunlaid process, polymer granules are melted and molten polymer is extruded through spinnerets. The continuous filaments are cooled and deposited on to a conveyor to form a uniform web. Some remaining temperature can cause filaments to adhere to one another, but this cannot be regarded as the principal method of bonding. The spunlaid process has the advantage of giving nonwovens greater strength, but raw material flexibility is more restricted. Co-extrusion of second components is used in several spunlaid processes, usually to provide extra properties or bonding capabilities. In meltblown web formation, low viscosity polymers are extruded into a high velocity airstream on leaving the spinneret. This scatters the melt, solidifies it and breaks it up into a fibrous web. Illustrations of these processes are for example provided on the Edana website: http://www.edana.org/discover-nonwovens/how-they're-made/formation.

These spunmelt multilayer nonwovens comprise a spunbond (S) layer, a meltblown layer (M) and a further spunbonded layer (S), to provide a composite fabric having desired physical and barrier properties. Nonwovens having multiple of these layers are also known for example SMMS or SMMMS multilayer nonwovens. The fibers forming the central layer may be made partially or entirely of a relatively resilient synthetic fibers, in particular polypropylene (PP), polyamide (PA, such as nylons) or polyethylene terephthalate (PET) fibers. The diameter of the fibers may for example range from 0.01 mm to 0.50 mm. More generally the acquisition layer material may be a multilayer material comprising different layers having different properties.

Typically the acquisition material in which the stretch openings are formed is homogenous in both transversal direction and longitudinal direction, especially regarding its thickness, basis weight and density. The acquisition material may for example have a basis weight ranging from 10 gsm to 500 gsm, in particular from 15 gsm to 200 gsm, and a thickness ranging from 0.25 mm to 5.00 mm, for example 0.5 mm to 3.0 mm, as measured at a pressure of 4.14 kPa (according to the test method described further below), and/or for example having a density of from 0.2 g/cc to 1.5 g/cc. The density can be calculated by dividing the basis weight of the high loft layer by its thickness measured at a pressure of 4.14 kPa (see the method details further below in the "test procedure" section). The values indicated herein for the acquisition material before it is slit and stretched (and optionally stacked to increase its basis weight and thickness).

The acquisition material may also be a high loft nonwoven fibrous layer. The term "high loft" refers to low density bulky fabrics, as compared to flat, paper-like fabrics. High loft webs are characterized by a relatively low density. This means that there is a relatively high amount of void space between the fibers. The high loft nonwoven fibrous layer that be used in the invention may in particular have a density below 0.200 g/cc, in particular ranging from 0.015 g/cc to 0.150 g/cc, in particular from 0.030 g/cc to 0.100 g/cc, for example 0.065 g/cc.

Stretch Openings 521, 522

The stretch openings of the acquisition layer 52 are obtained by stretching the acquisition layer material to open it in desired areas. The acquisition material is typically provided as a continuous stream in machine direction (MD), for example by unwinding a roll of acquisition material, which is then stretched to provide openings in the layer at the desired emplacement, typically before individualizing and attaching the acquisition layer to other components of the article. Before the stretching step, slits or other weakness lines can be formed in the acquisition material to provide for a controlled opening of the layer in desired emplacements of the stretch openings.

Figure 4:
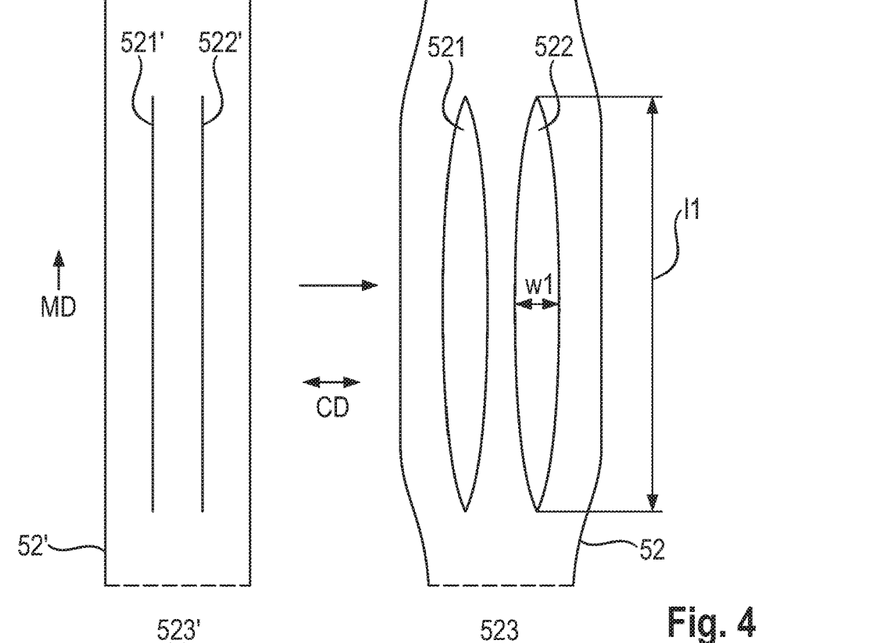
FIG. 4 shows schematically the process of stretching an acquisition layer which has been slit to provide a pair of stretch openings in the acquisition layer.

FIG. 4 illustrates the process of stretching an area 52' on a continuous stream of acquisition material to open slits 521', 522' to make stretch openings 521, 522. As schematically illustrated on FIG. 4, the acquisition layer material 52' can be first slit in machine direction to be provided with one or more slits 521', 522'. These slits can be cut in the acquisition material layer using one or more knives as is known in the art. The slits may be straight and oriented in machine direction (which may also typically correspond to the longitudinal direction of the article) as illustrated in the Figures, but it is not excluded that the slits could also be curved, undulating or otherwise not straight. After the slits are formed in the acquisition material, the acquisition material layer 52' is stretched in cross-direction (CD), i.e. perpendicular to the machine direction, to deform the acquisition material 52'. This stretch has for effect to open the slits in cross-direction, in particular the acquisition material is permanently deformed and the stretch openings are formed in the stretch acquisition material layer 52. The stretch openings typically have an elongated, oblong shape, as illustrated on FIG. 4 for example.

The dotted lines at the front and back of the acquisition material on FIGS. 4-5 highlight where the stream of acquisition material is later cut in cross-direction (CD) to individualize the acquisition layers. This cut in cross-direction will typically be conducted for simplicity after the stretch openings are formed. In other words the process of slitting and stretching the acquisition material take place continuously before individualizing the discrete acquisition layers. However it is not excluded that the step of individualizing the acquisition layers is performed before the stretching and opening step, in other words that the discrete acquisition layers are stretched individually.

Advantageously, at least one of the stretch openings 521, 522 obtained has a length 11 as measured in the longitudinal direction which is at least 25% of the length L of the article, in particular at least 33% of the length of the article. The maximum width (w1) of the stretch openings as measured in the stretch direction may be in particular at least 2 mm, or at least 3 mm, or at least 4 mm and up to 20 mm, or up to 15 mm, or up to 10 mm.

The stretch openings are collectively advantageously present along at least 50%, or at least 60%, or at least 70%, or at least 80% of the length of the acquisition layer. The stretch openings may be spaced from each other in the transversal direction by a minimum distance. This minimum distance may be for example at least 2 mm, in particular 5 mm. These dimensions may provide a more recognizable three-dimensional profile on the wearer-facing side of the article. The maximum and minimum width of each stripe as well as the other dimensions of the stripes may of course be varied according to the desired three-dimensional appearance of the wearer-facing side.

Typically at least one, in particular a pair, of the stretch openings are entirely surrounded by acquisition material encompassed in the acquisition layer 52, in other words are not extending to any of the front, back and/or longitudinal edges of the acquisition layer. One or more slits, for example two slits 523' at the front and two slits 524' at the back of the acquisition layer material 52' as shown in FIG. 5, may be added so that the stretch openings are collectively present along a larger proportion of the acquisition material layer, in particular up to 100% (or up to 90%, or up to 80%) of the length of the acquisition layer. This is to minimize any necking effect (represented in FIG. 4 but not in FIG. 1) that may impact the stretched acquisition material layer in the areas not comprising a slit. By having stretch openings along a longer proportion of the acquisition layer material, when the acquisition material layer is stretched, the whole or at least a larger proportion of the acquisition material layer can be uniformly deformed in cross-direction, thus reducing this necking effect.

Figure 5:
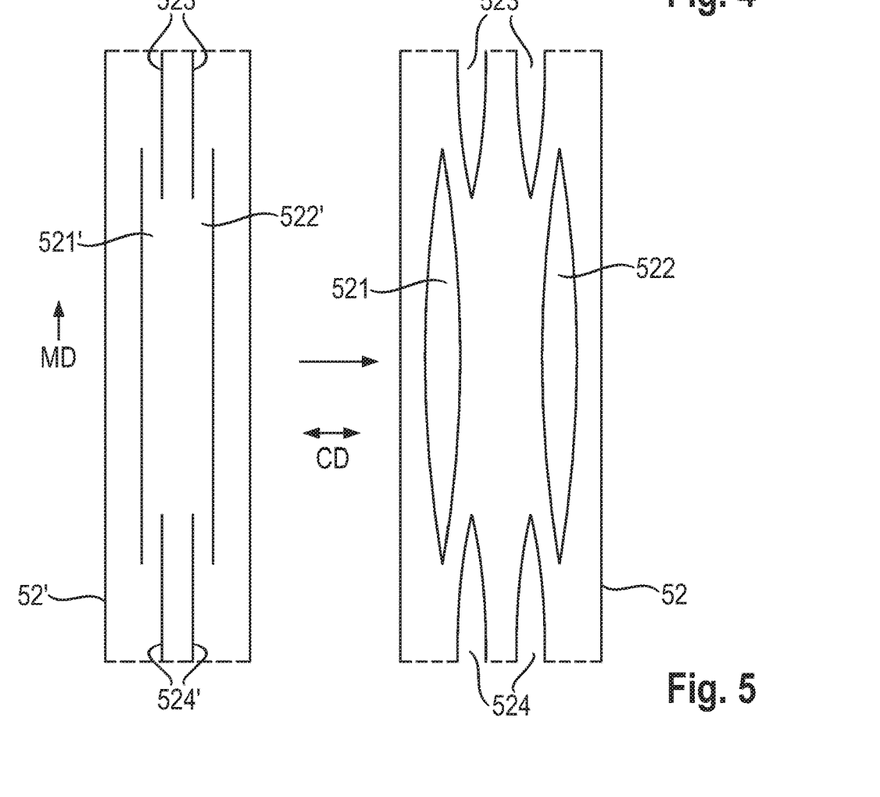
FIG. 5 shows schematically the same stretching process as FIG. 4, the acquisition layer comprising additional slits at the front and back of the acquisition layer.

Of course, the precursor acquisition material layer 52' shown in FIG. 4 and FIG. 5 is typically part of a continuous stream of material (not further represented) that is continuously slit or otherwise weakened in machine direction to form openable areas which are then stretched in cross-direction. The acquisition layers are individualized by cutting, typically in the cross-direction, the stretched acquisition material in a further step. The discrete acquisition material layers are then attached to the other components of the absorbent articles to make the absorbent articles. This of course takes place at high speed in a modern converting line with several hundred articles converted per minute. The term slits as used herein refers to configuration where the acquisition layer is cut through its entire thickness, but more generally any process step that sufficient weaken the acquisition material to provide openable areas in the acquisition layer material may be used, for example cutting through only a fraction of the thickness of acquisition material, making slits with intermittent cuts, providing energy through ultrasonic or heat localized application, etc. . . .

The article may also comprise two or more acquisition layers comprising matching stretch openings, to provide an even more profiling to the wearer-facing side of the article.

Additional Acquisition Layer 54

An additional acquisition layer 54 may be used in addition to the first acquisition layer described above. The material of the second acquisition material may be the same or different than the first acquisition material. For example a tissue layer may be placed between the first acquisition layer and the absorbent core. The tissue may have enhanced capillarity distribution properties compared to the acquisition layers described above. The first and the second acquisition layer may be of the same size or may be of different size, for example the second acquisition layer may extend further in the back of the absorbent article than the first acquisition layer. The additional acquisition layer 54 may be comprised of a single piece of material and may serve as a support for the first acquisition layer 52. The second acquisition layer may also serve to provide fluid acquisition properties in the area not covered by the first acquisition layer, in particular the areas of the stretch openings 521, 522. The additional acquisition layer may be in particular comprised of a single piece of material and the first acquisition layer 52 disposed on this single piece of second acquisition material. Any of the material as previously discussed for the first acquisition layer may be used for the second acquisition layer 54.

General Description of an Absorbent Core 28

The absorbent core 28 is the component of the article that has the maximum fluid retention capacity. The absorbent core comprises an absorbent material that is typically contained in a core wrap. Various constructions are possible. As used herein, the term "absorbent core" does not include the topsheet, the backsheet or a distribution/acquisition layer. The absorbent core comprises all or at least the majority of superabsorbent polymer (SAP) in the article. The core typically thus consists essentially of, or consists of, the core wrap, the absorbent material and optionally construction adhesives. The absorbent material may consist of a blend of SAP particles and cellulose fibers, but the invention is also applicable to other absorbent material for example consisting to 100% of SAP particles. The terms "absorbent core" and "core" are herein used interchangeably.

The absorbent material 60 may be any conventional absorbent material used in absorbent articles. The absorbent material usually comprises superabsorbent polymers (SAP) as is known in the art. The SAP is typically distributed in the form of small particles, which may be distributed in a matrix of cellulose fibers in so-called airfelt cores. The SAP typically represents from 40% to 70% of the weight of the absorbent material, the rest being cellulose and/or synthetic fibers. More recently, so called pulp-less or airfelt-free absorbent cores have been put on the market, wherein the absorbent material does not comprise cellulose fibers. In these airfelt-free cores, the SAP particles have been enclosed in pockets, see for example U.S. Pat. No. 5,433,715 (Tanzer et al.), WO2012/052172 (Van Malderen), or have been immobilized by a fibrous network of adhesive fibers (e.g. US2008/312617, Hundorf et al.). For example WO2008/155699 (Hundorf) discloses absorbent cores with a patterned layer of SAP immobilized by a net of fibrous thermoplastic adhesive material deposited over the layer of SAP.

The core wrap may be typically comprised of one sheet of core wrap material folded over the absorbent material or alternatively from two sheets of core wrap material forming respectively a top side and a bottom side of the core wrap, with suitable attachment along the longitudinal edges and optionally the front and back edges. The core wrap material is typically a low basis weight nonwoven (12 gsm or less). The top side of the core wrap may be treated to be more hydrophilic than the bottom side.

The overall footprint of the absorbent core is defined by the core wrap and is typically generally rectangular with a core width W' in the transversal direction and a core length L' in the longitudinal direction as measured from edge to edge, including the region of the core wrap which does not enclose the absorbent material, in particular at the front end seal and the back end seal when present. The width and length of the core may vary depending on the intended usage. For baby and infant diapers, the width W' may for example in the range from 40 mm to 200 mm and the length L' from 100 mm to 600 mm. Adult incontinence products may have higher maximum dimensions. The absorbent core may be symmetrical relative to the longitudinal axis 80. The longitudinal axis of the core typically overlaps with the longitudinal axis of the absorbent article when the core is incorporated in the article.

The absorbent material may be a blend of cellulose fibers with superabsorbent polymer (SAP) particles, also called absorbent gelling materials (AGM). The absorbent material may in particular comprise, by weight, from 30% to 75% of SAP particles, in particular from 40% to 70% by weight of SAP particles, or from 45% to 65% by weight of SAP particles relative to the total weight of absorbent material. The rest of the absorbent material may typically be cellulose fibers. The absorbent material may thus comprise from 25% to 70% by weight of cellulose fibers. Synthetic fibers may also be comprised in the absorbent core but are not typically considered as absorbent material. The absorbent material may also comprise higher amount of SAP, up to 75%, 80% by weight of the absorbent material, or more, mixed with cellulose or other fibers. The absorbent cores may also consist essentially of SAP without cellulose fibers as absorbent material (so called "airfelt-free" cores) as known in the art. For example WO2008/155699 (Hundorf) discloses absorbent cores with a patterned layer of SAP immobilized by a net of fibrous thermoplastic adhesive material deposited over the layer of SAP.

Suitable SAP may be any water-insoluble, water-swellable polymers capable of absorbing large quantities of fluids, as is known in the art. The term "superabsorbent polymer" refers herein to absorbent materials, typically cross-linked polymeric materials, that can absorb at least 10 times their weight of an aqueous 0.9% saline solution as measured using the Centrifuge Retention Capacity (CRC) test (EDANA method WSP 241.2.R3 (12)). The SAP may in particular have a CRC value of more than 20 g/g, or more than 24 g/g, or of from 20 to 50 g/g, or from 20 to 40 g/g, or 24 to 30 g/g.

The absorbent material 60 defines an absorbent material deposition area within the core wrap. The deposition area is delimited by the periphery of the absorbent layer formed by the absorbent material, as seen from above within the plane of the core. The deposition area may be generally rectangular as shown in the Figure, but it may also be advantageously shaped so that the longitudinal edges of the cores have a tapered section in the crotch region relative to the front region and/or back region, as is known in the art for so-called "shaped cores". Small size baby diapers may also comprise a notch on the front edge of the absorbent material's deposition area to adapt to the presence of remains of the umbilical cord of very small babies.

The absorbent material 60 may be deposited on one side of a core wrap material, with the other side of the core wrap being then applied on top of the absorbent layer thus deposited. The two sides of the core wrap may be made from a single substrate which is folded around the absorbent layer, or alternatively two different substrates may be used to form the first and the second sides of the core wrap respectively. Alternatively, the absorbent material may be deposited as a first and second absorbent layers applied on the top side 16 and bottom side 16' respectively with both absorbent layers then being brought in face to face contact and sandwiched together to form a unitary layer. This is for example disclosed in WO2008/155699 (Hundorf et al). The core wrap will be typically longitudinally sealed and optionally transversally sealed at its back and front edges.

The absorbent cores may also comprise macroscopic channels, which are absorbent material free areas encompassed within the deposition area. The top side and the bottom side of the core wrap may be bonded to each other through these channel areas. Absorbent cores having such channels are for example disclosed in WO2012/170778A1, Rosati et al., WO 2014/200794 A1, Bianchi et al. It is possible to provide the core with absorbent material free channels which are at least partially matching the stretch openings in the acquisition layer.

The absorbent cores of the present invention are not limited to a particular process for making them, and the cores of the invention may be more conventionally made by air-laying a mix of cellulose fibers and superabsorbent particles on a conventional air-laying drum fitted with raised portions matching the shapes of the desired channels so that that substantially no absorbent material is deposited in these areas. See for example WO2004/011723, Venturino et al. for a modified drum having raised portions to create areas having different basis weight. The shape of the raised portions may be adapted to make any desired channel shapes.

The absorbent core may have any caliper. Typically, the caliper of the core (dry, i.e. before use) as measured at the centerpoint point (C) or at any other points of the surface of the core according may range from 2.0 mm to 10.0 mm, in particular from 3.0 mm to 7.0 mm as measured at 2.07 kPa (0.30 psi) with a flat circular foot having a diameter of 17.0 mm (±0.2 mm).

Core Wrap 16, 16'

The absorbent core comprises a core wrap which encloses the absorbent material. The core wrap can typically comprise a substrate for receiving the absorbent material when the core is made. Various core wrap constructions are possible. The core wrap may in particular comprise as represented in the Figures two separate substrates 16, 16' forming the top side and the bottom side of the core wrap respectively. Having two different substrates for example allows more easily depositing an inner core glue on both the inner surface of the top side and the inner surface of the bottom side of the core wrap before combining these substrates to form the core wrap. The two substrates may be longitudinally attached in a C-wrap (as represented) or alternatively in a sandwich configuration with the two substrates in a face to face relationship for the two longitudinal seals. A front end seal and a back end seal may be optionally present. However this core wrap construction is not limiting of the invention, as any conventional core wrap construction may also be used, for example a single substrate on a portion of which the absorbent material is deposited and then the rest of the substrate folded over the deposited absorbent material to form the other side of the core. This single substrate construction can then be sealed longitudinally with a single longitudinal edge seal. The core wrap may also comprise two substrates disposed flat in a face to face relation (sandwich) with longitudinal side seals along their longitudinal sides.

The core wrap material may be any materials suitable for receiving and containing the absorbent material. Typical substrate materials used in the production of conventional cores may be used, in particular paper, tissues, films, wovens or nonwovens, or laminate of any of these. The core wrap may in particular be formed by a nonwoven web, such as a carded nonwoven, spunbond nonwoven ("S") or meltblown nonwoven ("M"), and laminates of any of these. For example spunmelt polypropylene nonwovens are suitable, in particular those having a laminate web SMS, or SMMS, or SSMMS, structure, and having a basis weight range of about 5 gsm to 15 gsm. Suitable materials are for example disclosed in U.S. Pat. No. 7,744,576, US 2011/0268932A1, US2011/0319848A1 and US2011/0250413A1. Nonwoven materials are typically made of synthetic fibers, such as PE, PET and in particular PP fibers. It is also possible than the core wrap may be at least partially formed from a component of the article having another function than merely serve as a substrate for the absorbent material. For example, it is possible that the backsheet may form the bottom side of the core wrap and/or that a distribution layer or the topsheet may form the top side of the core wrap. However, typically the core wrap is made of one or more substrates whose only or main function is to receive and enclose the absorbent material, as indicated previously.

As illustrated in FIG. 2, a first substrate 16 may substantially form the whole of the top side of the core wrap and a second substrate 16' substantially form the whole of the bottom side of the core wrap, but it is not excluded that this may be the other way around. By "substantially forming the whole of the surface", it is meant that if present, the outwardly extending flaps of the other substrate that have been folded longitudinally may also form part of the surface considered. The first substrate 16 may comprise two side flaps laterally extending along the length of the core and which are folded inwardly over each side edge of the absorbent core and the flaps may be attached to the outer surface of the second substrate for example by using an adhesive seal along each C-wrap seal. One or two continuous or semi-continuous lines of glue may be typically applied along the length of the flaps to bond the inner surface of the flaps to the external surface of the other substrate. The reverse construction may of course also be used with the bottom substrate forming flaps over the top substrate.

The core may also comprise so-called sandwich seals where the two substrates are bonded along one edge of the core to each other in face-to-face relationship with the inner surface of each substrate bonded to the inner surface of the other substrate. These sandwich seals can for example be formed using a hotmelt glue applied in a series of stripes in a direction perpendicular to the front and back edges of the core. These end seals are however optional as many absorbent cores are left open at the front and back ends. The longitudinal edges may also be bonded by such a sandwich seal.

Inner Core Glue

An inner core glue between the top side and bottom side of the core wrap is optional but advantageous. The inner core glue can improve the adhesion between the inner surfaces of the core wrap and the absorbent material. When present, the inner core glue may be applied directly over the inner surface of the top side and/or the inner surface of the bottom side of the core wrap to an area at least partially (e.g. at least 50% and up to 100%) corresponding to the deposition area of the absorbent material to at least partially immobilize the absorbent material. The inner core glue may be applied according to any known techniques, in particular it may be applied as a series of longitudinally-extending slots of glue as is known in the art, alternatively by other non-contact applicators such as spiral glue applicators, before the absorbent material is deposited on the nonwoven. The inner glue may thus be present in particular between the absorbent material and the inner surface of the bottom side of the core wrap, and/or between the absorbent material and the inner surface of the top side of the core wrap. An example of partial coverage of the deposition area by an inner core glue (also called auxiliary glue) to immobilize the absorbent material and to form channel bonds is for example disclosed in EP2,886,092 (Stelzig et al.). A fibrous thermoplastic material may also be present within the core wrap to help immobilizing the AGM particles, especially if the core is free of cellulose fibers. An inner glue is represented in FIG. 2 for example by the dotted lines between the top side of the core wrap and absorbent material.

Topsheet 24

The topsheet typically forms the majority of the wearer-contacting surface of the article and is the first layer that the body exudates contact. The topsheet is preferably compliant, soft-feeling, and non-irritating to the wearer's skin. Further, at least a portion of the topsheet is liquid permeable, permitting liquids to readily penetrate through its thickness. Any known topsheet may be used in the present invention. A suitable topsheet may be manufactured from a wide range of materials. Most topsheets are nonwoven materials or apertured formed films, but other materials are possible such as porous foams, reticulated foams, woven materials. Typical diaper topsheets have a basis weight of from about 10 gsm to about 28 gsm, in particular between from about 12 gsm to about 18 gsm but higher basis weights are possible if it is desired to provide a very soft feeling wearer-contacting surface for example.

Nonwoven topsheets may be made of natural fibers (e.g., wood or cotton fibers), synthetic fibers or filaments (e.g. polyester or polypropylene or bicomponent PE/PP fibers or mixtures thereof), or a combination of natural and synthetic fibers. If the topsheet includes nonwoven fibers, the fibers may be spunbond, carded, wet-laid, meltblown, hydroentangled, or otherwise processed as is known in the art. In particular the topsheet may be a spunbond PP nonwoven. A suitable topsheet comprising a web of staple-length polypropylene fibers is manufactured by Veratec, Inc., a Division of International Paper Company, of Walpole, Mass. under the designation P-8.

The topsheet may be of the type comprising a plurality of apertures. At least some of the apertures may have an area ranging from 1 $mm^2$ to 20 $mm^2$, and the topsheet may in particular comprise on average from 1 to 20 apertures per $cm^2$. The aperture ratio (the surface of all the apertures divided by the overall surface of the topsheet, measured when the topsheet is in a relaxed state, i.e. with just enough tension to smooth out any wrinkles) is advantageously in the range from 10% to 45%, in particular from 25% to 40%, more particularly from 30% to 35%. Typically, the total area of the apertures at the surface of a diaper may have an area of between about 10 cm$^2$ and about 50 cm$^2$, in particular between about 15 cm$^2$ and 35 cm$^2$. Examples of apertured topsheet are disclosed in U.S. Pat. No. 6,632,504 (Gillespie et at.).

WO 2011/163582 (Rinnert et al.) also discloses a suitable colored nonwoven topsheet having a basis weight of from 12 to 18 gsm and comprising a plurality of bonded points. Each of the bonded points has a surface area of from 2 mm$^2$ to 5 mm$^2$ and the cumulated surface area of the plurality of bonded points is from 10 to 25% of the total surface area of the topsheet.

The topsheet may also have a three-dimensional appearance and feel, or there may be an additional, smaller, three-dimensional layer placed on top of the topsheet. Such three-dimensional additional layers may be for example particularly useful to receive low viscous exudates such as the stool of young babies Examples of such fluid entangled dual layered three-dimensional materials and processes to obtain them have been disclosed for example in US2014/0121623A1, US2014/0121621A1, US2014/0121624A1, US2014/0121625A1. The topsheet may also be a formed film.

The topsheet may also be treated with a wetting agent to make it more hydrophilic. The wetting agent may be a surfactant as is known in the art. Other possible treatments are for example special coating by nanoparticles, as for example described in U.S. Pat. Nos. 6,645,569, 6,863,933, US2003/148684 and US2005/008839 (Cramer et al.) and U.S. Pat. No. 7,112,621 (Rohrbaugh et al). Any portion of the topsheet may also coated with a lotion as is known in the art. Examples of suitable lotions include those described in U.S. Pat. Nos. 5,607,760, 5,609,587, 5,643,588, 5,968,025 and 6,716,441. The topsheet may also include or be treated with antibacterial agents, some examples of which are disclosed in WO95/24173. Further, the topsheet, the backsheet or any portion of the topsheet or backsheet may be embossed and/or matte finished to provide a more cloth like appearance.

Backsheet 25

The backsheet may be any backsheet known in the art for absorbent articles. The backsheet may be positioned directly adjacent the garment-facing surface of the absorbent core. The backsheet prevents, or at least inhibits, the exudates absorbed and contained therein from soiling articles such as bedsheets and undergarments. The backsheet is typically impermeable, or at least substantially impermeable, to liquids (e.g., urine). The backsheet may, for example, be or comprise a thin plastic film such as a thermoplastic film having a thickness of about 12 microns to about 51 microns. The basis weight of those films is usually as low as possible to save material costs, typically from 10 gsm to 30 gsm, in particular below 20 gsm. A covering low basis weight nonwoven may be attached to the external surface of the film to provide for a softer touch.

Suitable backsheet materials include breathable materials which permit vapors to escape from the absorbent article while still preventing, or at least inhibiting, exudates from passing through the backsheet. Example breathable materials may include materials such as woven webs, nonwoven webs, composite materials such as film-coated nonwoven webs, microporous films such as manufactured by Mitsui Toatsu Co., of Japan under the designation ESPOIR NO and by Tredegar Corporation of Richmond, Va., and sold under the designation EXAIRE, and monolithic films such as manufactured by Clopay Corporation, Cincinnati, Ohio under the name HYTREL blend P18-3097.

The film may include at least about 10 weight percent filler particles, for example filler particles that include calcium carbonate, so that wherein the film has been stretched in the machine direction, e.g. to at least about 150 percent, fractures are formed where said filler particles are located. The films may be biaxially stretched at least about 150 percent in the machine direction and a transverse direction to cause fractures to form where said filler particles are located. Breathable films may generally have Water Vapor Transmission Rates (WVTR) in excess of 300 grams per square meter per 24 hours. The WVTR may be measured by the Desiccant Method as indicated in ASTM E96/E96M-14.

U.S. Pat. No. 6,075,179 for example discloses a suitable multilayer film comprising: a core layer made from an extrudable thermoplastic polymer, the core layer having a first exterior surface and a second exterior surface, a first skin layer attached to the first exterior surface of said core layer to form the multilayer film, the multilayer film defining an overall thickness. The first skin layer defines a first skin thickness, and comprising less than about ten percent of said overall thickness. The overall thickness is not exceeding about 30 micrometers and the multilayer film is a liquid barrier and has a WVTR of at least 300 g/m2/24 hours.

The backsheet may further typically comprise a nonwoven on its most external side to improve softness. Exemplary laminates comprising a breathable film and a nonwoven layer are for example disclosed in WO2014/022,362A1, WO2014/022,652A1 and U.S. Pat. No. 5,837,352. The nonwoven web may in particular comprise a spunbond nonwoven web and/or a laminate of a spunbond nonwoven web and a meltblown nonwoven web. The laminate may also have a water vapor transmission rate of at least 300 g/m2/24 hours. U.S. Pat. No. 5,843,056 for example discloses substantially liquid impermeable, vapor permeable composite backsheet.

Fastening System 42, 44

The absorbent article may include a fastening system, especially when the article is a taped diaper as exemplified in FIG. 1. The fastening system can be used to provide lateral tensions about the circumference of the absorbent article to hold the absorbent article on the wearer. Such a fastening system is not necessary for pant articles such as training pants and adult incontinence pants since the waist region of these articles is already bonded and elasticized. The fastening system usually comprises a fastener 42 such as tape tabs, hook and loop fastening components, interlocking fasteners such as tabs & slots, buckles, buttons, snaps, and/or hermaphroditic fastening components, although any other known fastening means are generally acceptable. A landing zone 44 is normally provided on the front waist region of the article for the fastener 42 to be releasably attached. Some exemplary surface fastening systems are disclosed in U.S. Pat. Nos. 3,848,594, 4,662,875, 4,846,815, 4,894,060, 4,946,527, 5,151,092 and 5,221,274 (Buell). An exemplary interlocking fastening system is disclosed in U.S. Pat. No. 6,432,098. The fastening system may also provide a means for holding the article in a disposal configuration as disclosed in U.S. Pat. No. 4,963,140 (Robertson et al.)

The fastening system may also include primary and secondary fastening systems, as disclosed in U.S. Pat. No.

4,699,622 to reduce shifting of overlapped portions or to improve fit as disclosed in U.S. 5,242,436, 5,499,978, 5,507, 86, and 5,591,152.

Front and Back Ears 46, 40

The absorbent article may comprise front ears 46 and back ears 40 as is known in the art in taped diapers. Absorbent articles in pant chassis are already sealed along the waist edges typically do not require front ears and back ears. The ears can be integral part of the chassis, for example formed from the topsheet and/or backsheet as side panel. Alternatively, as represented in FIG. 1, they may be separate elements attached by gluing and/or heat embossing. The back ears 40 are optionally stretchable to facilitate the attachment of the tabs 42 on the landing zone 44 and maintain the taped diapers in place around the wearer's waist. The front ears 46 may also be optionally elastic or extensible to provide a more comfortable and contouring fit.

Barrier Leg Cuffs 34 and Gasketing Cuffs 32

Figure 3:
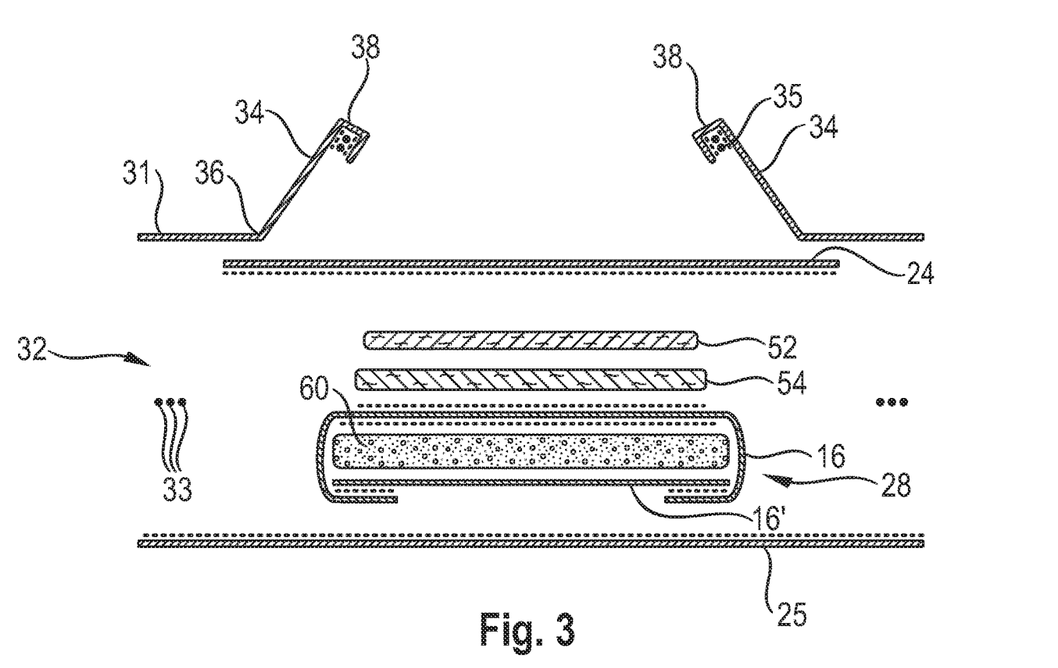
FIG. 3 shows a schematic transversal cross-section of the taped diaper of FIG. 1 at the front of the diaper outside the area of the stretch openings.

Absorbent articles such as taped diapers, training pants or adult incontinence pants may typically further comprise cuff components 30 that improve the fit of the article around the legs of the wearer. Such cuffs typically comprise barrier leg cuffs 34 and gasketing cuffs 32. The cuffs 30 may comprise a piece of material, typically a nonwoven, which is one side partially bonded to the article and on the other side can be partially raised away from the topsheet and thus stand up from the plane defined by the topsheet as shown for example in FIG. 3. Both parts of the cuffs may be advantageously elasticized. The raised part of the cuff components is referred to herein as barrier leg cuffs 34 and can provide improved containment of liquids and other body exudates approximately at the junction of the torso and legs of the wearer. The barrier leg cuffs 34 extend at least partially between the front edge and the back edge of the absorbent article on opposite sides of the longitudinal axis and are at least present adjacent to the center point C of the article.

The barrier leg cuffs 34 may be delimited by a proximal edge 37 joined to the rest of the article, typically the topsheet, and a free terminal edge 38 intended to contact and form a seal with the wearer's skin. The barrier leg cuffs 34 may be joined at the proximal edge 37 with the chassis of the article by a bond which may be made for example by adhesive bonding, fusion bonding or combination of known bonding means, for example as disclosed in WO2014/168810A1 (Bianchi et al.). The bond at the proximal edge 37 may be continuous or intermittent.

The barrier leg cuffs 34 can be integral with (i.e. formed from) the topsheet or the backsheet, or more typically be formed from a separate material joined to the rest of the article. Typically the material of the barrier leg cuffs may extend through the whole length of the article but is "tack bonded" to the topsheet towards the front edge and back edge of the article so that in these sections the barrier leg cuff material remains flush with the topsheet. Each barrier leg cuff 34 may comprise one, two or more elastic strings 35 close to its free terminal edge 38 to provide a better seal.

In addition to the barrier leg cuffs 34, the article may comprise gasketing cuffs 32, which are formed in the same plane as the chassis of the absorbent article, in particular may be at least partially enclosed between the topsheet and the backsheet, and typically placed further laterally outwardly relative to the barrier leg cuffs 34. The gasketing cuffs 32 can provide a better seal around the thighs of the wearer. Usually each gasketing leg cuff 32 will comprise one or more elastic string or elastic element 33 comprised in the chassis of the diaper for example between the topsheet and backsheet in the area of the leg openings. Typically the barrier leg cuffs 34 are disposed more internally than the gasketing cuffs 32. The barrier leg cuffs are thus also referred to as inner cuffs and the gasketing cuffs as outer cuffs.

For example, U.S. Pat. No. 3,860,003 describes a disposable diaper which provides a contractible leg opening having a side flap and one or more elastic members to provide an elasticized leg cuff (a gasketing cuff). U.S. Pat. No. 4,808, 178 (Aziz) and U.S. Pat. No. 4,909,803 (Aziz) describe disposable diapers having "stand-up" elasticized flaps (barrier leg cuffs) which improve the containment of the leg regions. U.S. Pat. No. 4,695,278 (Lawson) and U.S. Pat. No. 4,795,454 (Dragoo) describe disposable diapers having dual cuffs, including gasketing cuffs and barrier leg cuffs. All or a portion of the barrier leg and/or gasketing cuffs may be treated with a lotion.

Other Components

The absorbent articles of the invention can further comprise any other typical components known for the intended purpose of the article that are not illustrated in the Figures, such as a transverse barrier element extending across the topsheet to form a receptacle for bowel movement, a lotion application on the topsheet, a wetness indicator comprising a pH indicator disposed between the absorbent core and the backsheet, etc. These components are well-known in the art and will not be further discussed herein. Reference is made to WO2014/093310 where several examples of these components are disclosed in more details.

The absorbent article may also comprise an elastic waist band (also called elastic waist feature) disposed parallel to and along the back edge of the article and/or less commonly parallel to and along the front edge of the article. Such waistbands help providing improved fit and containment at the back and/or front edge of the article. The elastic waist feature is generally intended to elastically expand and contract to dynamically fit the wearer's waist. The elastic waist band may be constructed in a number of different configurations. Non-limiting examples of back and front waistbands can be found in WO2012/177400 and WO2012/177401 (Lawson), and U.S. Pat. Nos. 4,515,595, 4,710,189, 5,221, 274 and 6,336,922 (VanGompel et al.).

Pant-Like Articles

As indicated previously, the invention may be also used in absorbent articles presented in the form of a pant or underwear (herein "pant"). In these articles, the waist and the leg openings are pre-formed during manufacture so that the article can be put on like underwear. These pant articles typically have a front waist panel and a back waist panel which are sealed together via side seams. The side seams can be broken to remove and discard the article and are typically not re-fastenable. The front and back waist panels are typically elasticized. Pants are used as taped diapers on babies and younger children for day wear and for overnight dryness, as training pant for older children at the toilet training stage, and also as adult incontinence protection.

Pant-like articles typically comprise a front waist panel and a back waist panel joined together via side seams to form the waist opening and at least part of the leg openings. The waist panels are typically elasticized, either using a material which is inherently elastic to make them (such as a laminate comprising an elastomeric layer between two nonwoven layers) or by sandwiching a plurality of elastic strands between two nonwovens along the width of the panels, as is known in the art. The pants also typically comprises a chassis comprising the remaining components of the article, in particular the topsheet, the backsheet, the absorbent core and barrier cuffs including upstanding barrier leg cuffs and attached on one side to the front waist panel and on the other side of the back waist panel. These components may be generally constructed as in previously disclosed for the taped diaper.

Packages

A plurality of articles according to the invention may be packaged in a package for transport and sale. At least 50% of the articles, and preferably all the articles, in the package may be according to the invention. The articles may be folded and packaged as is known in the art. The package may be for example a plastic bag or a cardboard box. Diapers may typically bi-folded along the transversal axis and the ears folded inwardly before being packaged. The absorbent articles may be packed under compression so as to reduce the size of the packages, while still providing an adequate amount of absorbent articles per package. By packaging the absorbent articles under compression, caregivers can easily handle and store the packages, while also providing distribution and inventory savings to manufacturers owing to the size of the packages.

Packages of the absorbent articles of the present disclosure may in particular have an In-Bag Stack Height of less than 110 mm, less than 105 mm, less than 100 mm, less than 95 mm, less than 90 mm, specifically reciting all 0.1 mm increments within the specified ranges and all ranges formed therein or thereby, according to the In-Bag Stack Height Test. The method used to measure the In-Bag Stack Height is described in further details in WO2017/023656 (Weisman et Al.). For each of the values indicated in the previous sentence, it may be desirable to have an In-Bag Stack Height of greater than 60, or greater than 70 mm, or greater than 75 mm, or greater than 80 mm.

The absorbent articles may thus be packaged compressed at an In-Bag Compression Rate of at least 10%, in particular of from 10% to 50%, in particular from 20% to 40%. The "In-Bag Compression Rate" as used herein is one minus the height of a stack of 10 folded articles measured while under compression within a bag ("In-Bag Stack Height") divided by the height of a stack of 10 folded articles of the same type before compression, multiplied by 100; i.e. (1-In-Bag Stack Height/stack height before compression)*100, reported as a percentage. Of course, the stack in the bag does not need to have exactly 10 articles, rather the value measured for the height of stack of article in the package is divided by the number of articles in the stack and then multiplied by 10. The articles before compression are sampled from the production line between the folding unit and the stack packing unit. The stack height before compression is measured by taking 10 articles before compression and packing, and measuring their stack height as indicated for the IBSH.

Process for Making

The topsheet 24, the backsheet 25, the absorbent core 28, the acquisition layer 52 and the other article components may be assembled in a variety of well-known configurations. Typically, adjacent layers will be joined together using conventional bonding method such as adhesive coating via slot coating or spraying on the whole or part of the surface of the layer, or thermo-bonding, or pressure bonding or combinations thereof. Most of the bonding between components is for clarity and readability not represented in the Figure, except in the cross-sectional views wherein some of the glue layers are indicated by dotted lines. Bonding between the layers of the article should be considered to be present unless specifically excluded. Adhesives may be typically used to improve the adhesion of the different layers, for example between the backsheet and the core wrap. The adhesives used may be any standard hotmelt glue as known in the art. The individual components may be converted into an absorbent article according to any of the processes known in the art.

At least one portion the topsheet can be attached directly or indirectly to an underlying layer such as the top side of the absorbent core or a second acquisition layer through at least one of the stretch openings of the acquisition layer. The topsheet may thus be bonded directly or indirectly to the top side of the absorbent core through these openings for example by adhesive bonding (gluing). Indirect bonding of the topsheet to an underlying layer may be for example provided when a second acquisition layer not comprising stripes is present between the topsheet and the first acquisition layer comprising the stripes.

More generally, the articles of the invention may be continuously made on a converting line, the process comprising the steps of:

providing a continuous stream of an acquisition material;
weakening the acquisition material in discrete areas to form openable areas;
stretching the acquisition material to open the one or more openable areas thus forming stretch openings in the acquisition material;
cutting the acquisition material into discrete acquisition layers;
attaching the discrete acquisition layers to the other components of the absorbent articles to make absorbent articles, wherein each acquisition layer comprises at least one stretch opening.

As indicated previously, the stream of acquisition material may be slit using a straight knife (typically mounted on a rotating roll) but the slits may also be non-straight such as curved or undulating. The slits or otherwise formed openable areas are generally oriented in machine direction of the stream of continuous material, which is typically the same orientation as the longitudinal direction of the finished article, and the acquisition material is stretched in cross direction, the stretch direction may correspond to the transversal direction of the articles in which the discrete acquisition layers are then converted.

Test Procedures

The values indicated herein are measured according to the methods indicated herein below, unless specified otherwise. All measurements are performed at 21° C.±2° C. and 50%±5% RH, and samples should be kept at least 24 hours in these conditions to equilibrate before conducting the tests, unless indicated otherwise. For example the Static Peel Force Time is measured at 23 degrees as is indicated below.

Centrifuge Retention Capacity (CRC)

The CRC measures the liquid absorbed by the superabsorbent polymer particles for free swelling in excess liquid. The CRC is measured according to EDANA method WSP 241.2.R3 (12).

Recesses Depth Measurement Method

The depth of the recesses formed at the wearer-facing surface of the article by the topsheet folding in the stretch openings can be measured according to the following method. The article is gently pulled and held flat as illustrated in FIG. 1 (a closed article of the pant type can be opened at the side seams). If the topsheet is attached through the stretch openings within the recesses to an underlying layer, a non-contact measurement method using a laser caliper is used to measure the depth (d1) of the recess relative to the neighboring areas. The depth of each recess is measured in the transversal middle of the recesses relative to the neighboring acquisition material. If the acquisition material has a varying thickness in the transversal direction, the depth of the recess is measured relative to each side of the recess (i.e. between two stretch openings, or between the stretch opening and a lateral side of the acquisition layer and in the middle of the zone of the material considered) and the highest depth value is recorded (however typically the acquisition layer has an about constant thickness),). The measurement can be made at different representative points along the length of the recesses and the maximum value obtained is recorded as the depth of the recess (however typically the depth of the recess is about constant along the recess and can be simply measured in the middle of the recess).

If the topsheet is not attached or only loosely attached to the underlying layer through the openings, a contact method using a small probe is used instead. The depth is measured using a foot and anvil type digital caliper such as an Ono Sokki GS 503/DG 3610 caliper gage or equivalent. The instrument is operated and calibrated as per the manufacturer's instructions. The tip of the foot has a 3 mm diameter hall foot which applies a downward force of 30.0 g. The measurements are made as indicated in the previous paragraph, the depth is calculated by taking the depth measured by the probe in the middle of the recess relative to the height of the neighboring acquisition material al the same longitudinal position. The depth of the recesses can be measured at representative points along the recess to determine the maximum depth of the recess (however typically the depth of the recess is about constant along the recess).

Acquisition Layer Thickness and Density Measurement Method

This method is used to measure the thickness of the acquisition layer in a standardized manner. The density can then be calculated from the thickness and the basis weight.

Sample: The measurements is preferably made on the acquisition raw material to ensure good reproducibility and ease of sampling. If the raw material is not available, the measurements can be made on a carefully extracted acquisition material layer from a finished article, measuring in areas of the extracted layer that have not been modified by the converting to obtain a close approximation of the value of the raw material. The samples are kept at least 24 hours at 21° C.±2° C. and 50%±20% RH to equilibrate.

Equipment: standard testing gage (as described in NWSP 120.1R0 (15)), consisting of a dead-weight, calibrated spring force, or string gage type and having dimensions and capabilities specified below:

a) Presser foot, circular presser foot 25.40±0.02 mm diameter.
b) Anvil, 38 mm diameter or greater.
c) Anvil/presser foot parallelism, 0.01 mm.
d) Foot surface parallelism, 0.002 mm.
e) Applied force, 4.14±0.21 kPa.
f) Readability, 0.02 mm.
g) Automatic, microprocessor data gathering systems, (optional).

Procedure: The thickness gage is calibrated as directed in the manufacturer's instructions. The sample is laid flat on the anvil with the bottom side (the side placed towards the backsheet in the finished article) facing down and with the center of the acquisition layer placed directly under the center of the presser foot. The presser foot is gently brought into contact with the top side of the sample and the pressure is gradually increased to the specified level. Allow approximatively 5s at the full pressure before releasing the foot and record the thickness value to the nearest 0.2 mm 5s to 6s after the full pressure has been applied.

Ten samples are measured in this manner for a given type of articles and the average caliper is calculated and reported with an accuracy of one tenth mm. The basis weight of each sample is calculated by dividing the weight of each sample by their area.

The density, in g/cc, is calculated by dividing the basis weight (in $g/cm^2$) of the material by the thickness (in cm).

In-Bag Stack Height Test

The In-Bag Stack Height of a package of absorbent articles is determined as follows:

Equipment: A thickness tester with a flat, rigid horizontal sliding plate is used. The thickness tester is configured so that the horizontal sliding plate moves freely in a vertical direction with the horizontal sliding plate always maintained in a horizontal orientation directly above a flat, rigid horizontal base plate. The thickness tester includes a suitable device for measuring the gap between the horizontal sliding plate and the horizontal base plate to within ±0.5 mm. The horizontal sliding plate and the horizontal base plate are larger than the surface of the absorbent article package that contacts each plate, i.e. each plate extends past the contact surface of the absorbent article package in all directions. The horizontal sliding plate exerts a downward force of 850±1 gram-force (8.34 N) on the absorbent article package, which may be achieved by placing a suitable weight on the center of the non-package-contacting top surface of the horizontal sliding plate so that the total mass of the sliding plate plus added weight is 850±1 grams. Such a testing apparatus is for example illustrated on FIG. 19 of US2008/0312624A1.

Test Procedure: Absorbent article packages are equilibrated at 21±2° C. and 50±5% relative humidity prior to measurement. The horizontal sliding plate is raised and an absorbent article package is placed centrally under the horizontal sliding plate in such a way that the absorbent articles within the package are in a horizontal orientation. Any handle or other packaging feature on the surfaces of the package that would contact either of the plates is folded flat against the surface of the package so as to minimize their impact on the measurement. The horizontal sliding plate is lowered slowly until it contacts the top surface of the package and then released. The gap between the horizontal plates is measured to within ±0.5 mm ten seconds after releasing the horizontal sliding plate. Five identical packages (same size packages and same absorbent articles counts) are measured and the arithmetic mean is reported as the package width. The "In-Bag Stack Height"=(package width/absorbent article count per stack)×10 is calculated and reported to within ±0.5 mm.

Misc

As used herein, the terms "comprise(s)" and "comprising" are open-ended; each specifies the presence of the feature that follows, e.g. a component, but does not preclude the presence of other features, e.g. elements, steps, components known in the art or disclosed herein. These terms based on the verb "comprise" should be read as encompassing the narrower terms "consisting essentially of" which excludes any element, step or ingredient not mentioned which materially affect the way the feature performs its function, and the term "consisting of" which excludes any element, step, or ingredient not specified. Any preferred or exemplary embodiments described below are not limiting the scope of the claims, unless specifically indicated to do so. The words "typically", "normally", "preferably", "advantageously", "in particular", "optionally" and the likes also qualify features which are not intended to limit the scope of the claims unless specifically indicated to do so.

Unless indicated otherwise, the description and claims refer to the absorbent core and article before use (i.e. dry, and not loaded with a fluid) and conditioned at least 24 hours at 21° C.+/−2° C. and 50+/−5% Relative Humidity (RH).

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article for personal hygiene comprising a wearer-facing side, a garment-facing side, and a longitudinal axis, the absorbent article having a first length measured along the longitudinal axis, the absorbent article comprising:
    a liquid permeable topsheet on the wearer-facing side;
    a liquid impermeable backsheet on the garment-facing side;
    an absorbent core between the topsheet and the backsheet; and
    an acquisition layer between the topsheet and the absorbent core;
    wherein the acquisition layer comprises one or more stretch openings;
    wherein the one or more stretch openings each have a second length measured along the longitudinal axis;
    wherein the second length is at least 33% of the first length; and
    wherein at least a portion of the topsheet is attached through at least one of the stretch openings to an underlying layer.

2. The absorbent article according to claim 1, wherein each of the one or more stretch openings is present along at least 50% of a longitudinal length of the acquisition layer.

3. The absorbent article according to claim 2, wherein the acquisition layer comprises two stretch openings disposed symmetrically relative to the longitudinal axis.

4. The absorbent article according to claim 1, wherein a portion of the topsheet is at least partially positioned within at least one of the stretch openings so that the portion of the topsheet forms a recess on the wearer-facing side.

5. The absorbent article according to claim 4, wherein the recess has a depth of at least 0.25 mm, as measured from the wearer-facing side.

6. The absorbent article according to claim 1, wherein at least one of the stretch openings does not extend to any edges of the acquisition layer.

7. The absorbent article according to claim 6, wherein at least one of the stretch openings extends to a front edge and/or a back edge of the acquisition layer.

8. The absorbent article according to claim 1, wherein the acquisition layer does not comprise superabsorbent particles, and wherein the absorbent article comprises an additional acquisition layer between the topsheet and the absorbent core.

9. The absorbent article according to claim 1, wherein the absorbent core comprises one or more channels.

10. A package comprising a plurality of absorbent articles according to claim 1.

* * * * *